United States Patent
Mao

(10) Patent No.: US 11,993,808 B2
(45) Date of Patent: May 28, 2024

(54) EXPERIMENTAL APPARATUS FOR BIOCHIP

(71) Applicants: BEIJING BOE TECHNOLOGY DEVELOPMENT CO., LTD., Beijing (CN); BOE TECHNOLOGY GROUP CO., LTD., Beijing (CN)

(72) Inventor: Defeng Mao, Beijing (CN)

(73) Assignees: BEIJING BOE TECHNOLOGY DEVELOPMENT CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 919 days.

(21) Appl. No.: 17/040,306

(22) PCT Filed: Apr. 7, 2020

(86) PCT No.: PCT/CN2020/083431
§ 371 (c)(1),
(2) Date: Sep. 22, 2020

(87) PCT Pub. No.: WO2020/224363
PCT Pub. Date: Nov. 12, 2020

(65) Prior Publication Data
US 2021/0147921 A1   May 20, 2021

(30) Foreign Application Priority Data

May 6, 2019   (CN) .......................... 201920639813.3

(51) Int. Cl.
*C12Q 1/68* (2018.01)
*B01L 3/00* (2006.01)
*C12Q 1/6837* (2018.01)

(52) U.S. Cl.
CPC ............ *C12Q 1/6837* (2013.01); *B01L 3/502* (2013.01); *B01L 2300/0636* (2013.01); *B01L 2300/0877* (2013.01)

(58) Field of Classification Search
CPC .................. C12Q 1/6837; B01L 3/502; B01L 2300/0636; B01L 2300/0877
See application file for complete search history.

(56) References Cited

U.S. PATENT DOCUMENTS

| | | | | |
|---|---|---|---|---|
| 8,828,712 B2 * | 9/2014 | Amano | ............... | B01L 3/50851 |
| | | | | 435/283.1 |
| 9,359,638 B2 * | 6/2016 | Takahashi | ............ | C12Q 1/6825 |
| 10,322,234 B2 * | 6/2019 | Blundred | ............ | A61M 5/2448 |

FOREIGN PATENT DOCUMENTS

| | | |
|---|---|---|
| CN | 1256415 A | 6/2000 |
| CN | 101539570 A | 9/2009 |
| CN | 103255054 A | 8/2013 |
| CN | 104198468 A | 12/2014 |
| CN | 208313834 U | 1/2019 |
| CN | 209872930 U | 12/2019 |

OTHER PUBLICATIONS

"Working principle of temperature controller", www.elecfans.com/yuanqijian/kaiguan/20171101573665.html, Nov. 1, 2017.
"The control principle of Siemens S7-300PLC temperature module", www.douban.com/note/485654179/, Feb. 25, 2015.

* cited by examiner

*Primary Examiner* — Stephanie K Mummert
(74) *Attorney, Agent, or Firm* — DINSMORE & SHOHL LLP

(57) ABSTRACT

The present disclosure relates to an experimental apparatus for a biochip comprising: an enclosure within which a chamber configured to hold the biochip and a solution is disposed, wherein the enclosure is provided with an observation area, for observing a reaction process of the biochip and the solution in the chamber during an experiment.

15 Claims, 4 Drawing Sheets

EXPERIMENTAL APPARATUS FOR BIOCHIP

CROSS-REFERENCE TO RELATED APPLICATIONS

This application is a U.S. National Stage under 35 U.S.C. § 371 of International Application No. PCT/CN2020/083431, as filed on Apr. 7, 2020, which claims the priority to the Chinese Patent Application No. 201920639813.3 filed on May 6, 2019. The disclosure of each of these applications is incorporated by reference herein in its entirety.

TECHNICAL FIELD

The present disclosure relates to the technical field of biological equipment, and more particularly, to an experimental apparatus for a biochip.

BACKGROUND

With the rapid development of the modern gene chip detection technology, it has increasingly wide applications in fields of functional gene research, new drug screening, gene diagnosis of diseases, and the like. The gene chip detection is a complex process, including: amplification of target gene, labeling of probe, hybridization and cleaning of chip, detection and analysis of hybridization signal, etc. Common detection methods include:
1. hybridization by using sampling and cover glass, which is to put the gene chip in a hybridization box and then put it in a water bath at a certain temperature for static hybridization;
2. hybridization by using a flow path-based automatic hybridization instrument; and
3. hybridization with the biochip by using an integrated hybridization box.

None of the three detection methods can perform real-time monitoring during the experiment process, and the gene chip can be taken out for observation only after the experiment is completed.

SUMMARY

An experimental apparatus for a biochip provided by the embodiments of the present disclosure comprises: an enclosure within which a chamber configured to hold the biochip and a solution is disposed, wherein the enclosure is provided with an observation area, for observing a reaction process of the biochip and the solution in the chamber during an experiment.

Alternatively, the enclosure is a split structure.

Alternatively, the enclosure comprises: a first pressing block, and a second pressing block opposing the first pressing block, wherein a side of the first pressing block facing the second pressing block is provided with a first reaction groove, a side of the second pressing block facing the first pressing block is provided with a second reaction groove, the first pressing block and the second pressing block are detachably fixed together, and the first reaction groove and the second reaction groove encircle to form the chamber.

Alternatively, the enclosure further comprises: a sealing cover mounted within one of the first reaction groove and the second reaction groove, and having an opening end facing the other of the first reaction groove and the second reaction groove, wherein the biochip is pressed against the other of the first reaction groove and the second reaction groove through the opening end of the sealing cover during the experiment, and the chamber formed by the encircling of the sealing cover and the biochip is used to define the solution.

Alternatively, the enclosure further comprises: a mounting cover mounted within the one of the first reaction groove and the second reaction groove, an opening of the mounting cover facing the other of the first reaction groove and the second reaction groove, and the sealing cover mounted within the mounting cover.

Alternatively, a positioning lug is arranged on the mounting cover, the positioning lug penetrates through one of the first pressing block and the second pressing block corresponding to the one of the first reaction groove and the second reaction groove to protrude out, a fitting lug is arranged on the corresponding one of the first pressing block and the second pressing block, and the positioning lug and the fitting lug are fixed together.

Alternatively, the sealing cover is made of transparent epoxy resin, the mounting cover is made of transparent glass, and the observation area is an observation window located on one of the first pressing block and the second pressing block corresponding to the one of the first reaction groove and the second reaction groove.

Alternatively, the experimental apparatus further comprises: a connecting member, one end of which penetrates through the first pressing block and the second pressing block, and the other end of which is provided with a limiting part; and a spring and a locking member, wherein the spring is sleeved on the connecting member, the locking member is fixed to the one end of the connecting member, and the spring presses against the first pressing block and the second pressing block.

Alternatively, the connecting member is a bolt, and the locking member is a nut.

Alternatively, the experimental apparatus further comprises: a constant temperature module mounted on the enclosure and configured to keep a temperature within the chamber to be constant during the experiment.

Alternatively, the constant temperature module includes a heat sink mounted on a wall of the chamber and configured to keep the temperature within the chamber to be constant.

Alternatively, the enclosure is provided with a through hole in communication with the chamber.

Alternatively, the through hole includes at least one of a liquid inlet hole, a liquid outlet hole and a liquid feeding hole.

Further features of the present disclosure and advantages thereof will be set forth in the following description, and in part will become obvious from the description, or will be learned by the practice of the present disclosure. The objectives and other advantages of the present disclosure may be achieved and attained by the structure particularly pointed out in the description and the claims as well as the accompanying drawings.

BRIEF DESCRIPTION OF THE DRAWINGS

The accompanying drawings, which constitute a part of the specification, provide further understanding of the technical solutions of the present disclosure, and together with the embodiments of the present application, serve to explain the technical solutions of the present disclosure but do not limit them.

DETAILED DESCRIPTION

To make the objectives, technical solutions and advantages of the present disclosure more apparent, embodiments of the present disclosure will be described in detail below with reference to the accompanying drawings. It should be noted that the embodiments in the present application and features in the embodiments may be arbitrarily combined with each other without conflict.

In the following description, numerous specific details are set forth in order to provide a thorough understanding of the present disclosure, however, the present disclosure may be practiced otherwise than as specifically described herein, and thus the scope of protection of the present disclosure is not limited by the specific embodiments disclosed below.

The three detection methods in the related art have the following problems: the hybridization process cannot be observed during the experiment, and the gene chip can be taken out for observation only after the experiment is completed, and other problems also exist as follows:

1. In the hybridization by using sampling and cover glass, since because the temperature consistency of the water bath is unstable, the hybridization signal is often uneven;
2. In the hybridization by using a flow path-based automatic hybridization instrument, since more hybridization solution is needed in one experiment process, the experiment cost is increased; and
3. In the hybridization with the biochip by using an integrated hybridization box, since the hybridization box is disposable and cannot be reused, the experiment cost is increased.

Compared with the related art, the experimental apparatus for a biochip provided by the present disclosure can observe the reaction condition of the biochip and the solution through the observation area during the experiment, can perform real-time monitoring, and can observe the working process and result of the biochip without the need of taking out the biochip. Moreover, a volume of the chamber can be designed smaller, and an amount of the solution used during the experiment is then less, which can reduce the experiment cost.

The experimental apparatus for a biochip provided by the embodiments of the present disclosure, as shown in FIGS. 1 to 5, comprises: an enclosure, and a chamber 1 formed inside the enclosure and configured to hold the biochip and a solution, wherein the enclosure is provided with an observation area for observing a reaction process of the biochip and the solution during an experiment.

The experimental apparatus can observe the reaction condition of the biochip and the solution through the observation area during the experiment, can perform real-time monitoring, and can observe the working process and result of the biochip without the need of taking out the biochip. Moreover, the volume of the chamber 1 can be designed smaller, and the amount of the solution used during the experiment is then less, which can reduce the experiment cost.

Figure 1:
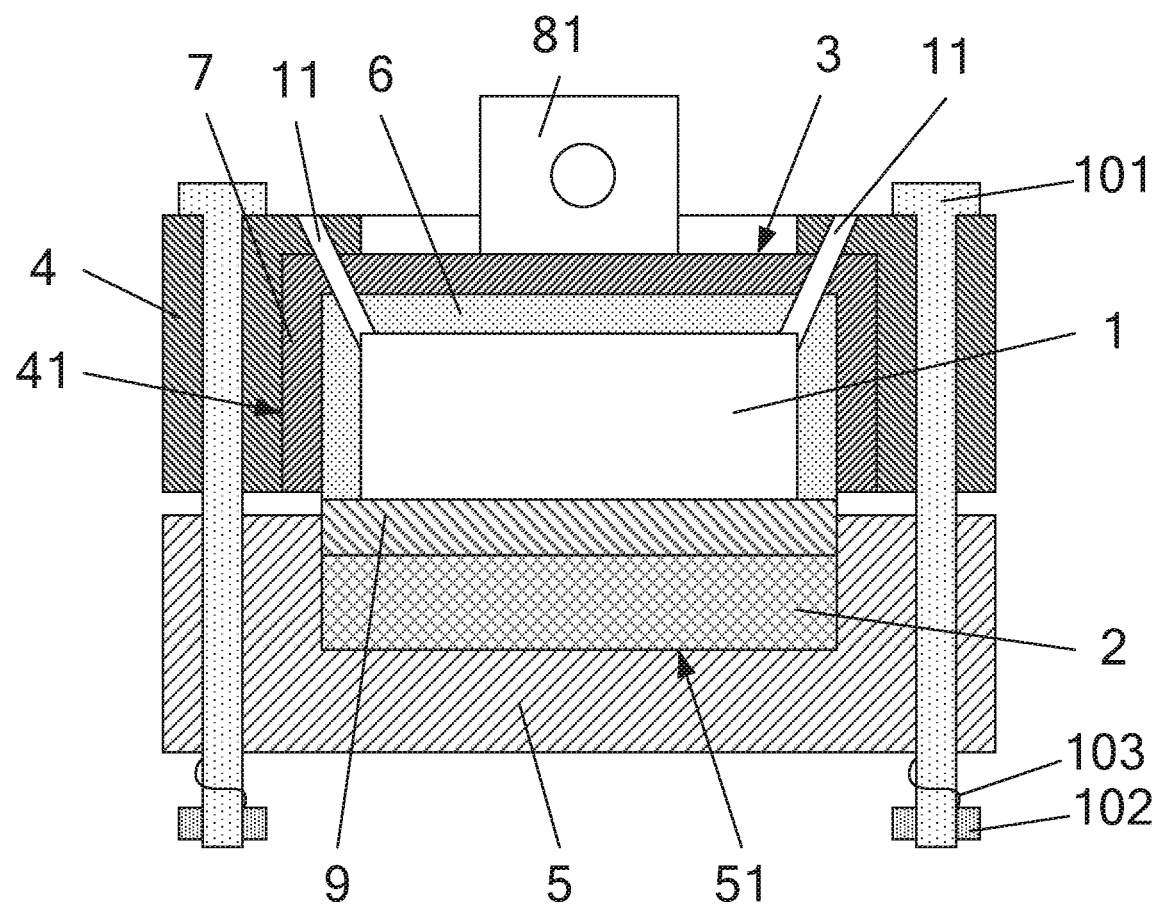
FIG. 1 is a sectional schematic view of an experimental apparatus for a biochip according to an embodiment of the present disclosure after a gene chip is mounted thereon.
Figure 4:
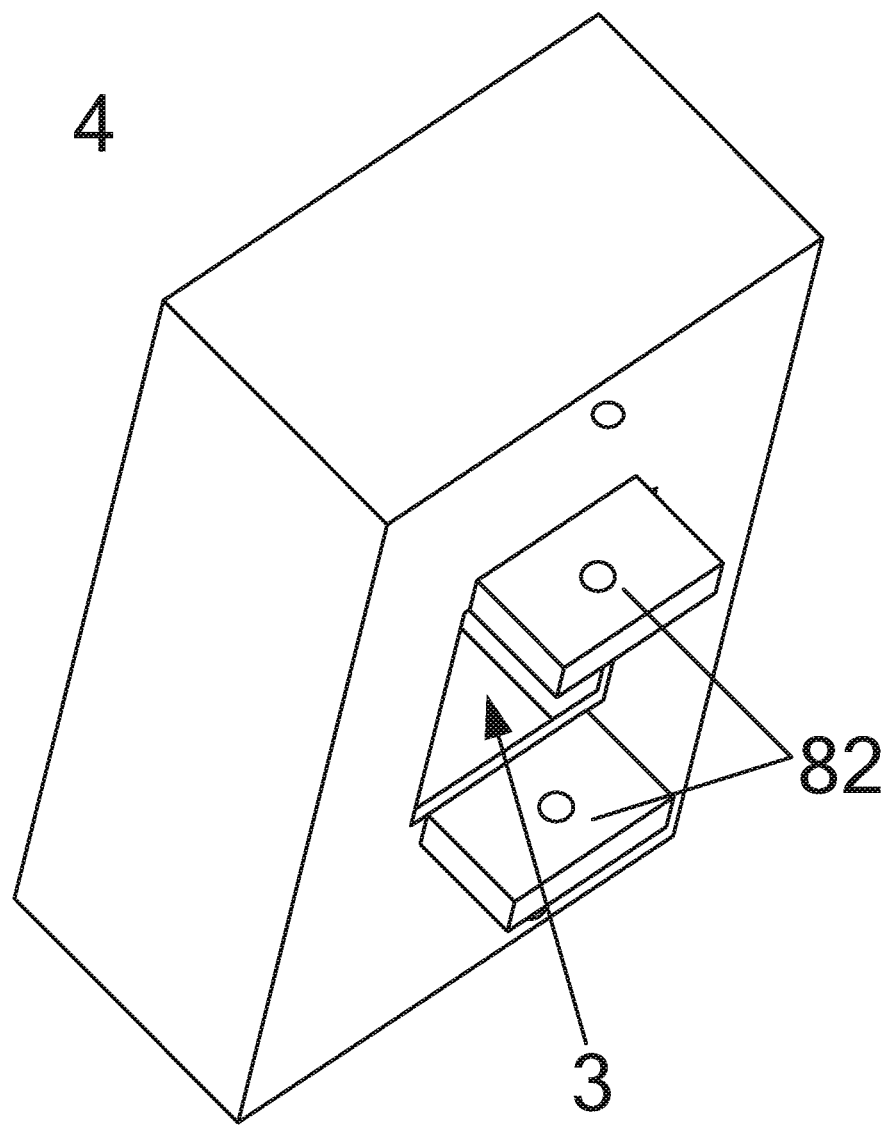
FIG. 4 is a perspective schematic view of the first pressing block of FIG. 1.
Figure 5:
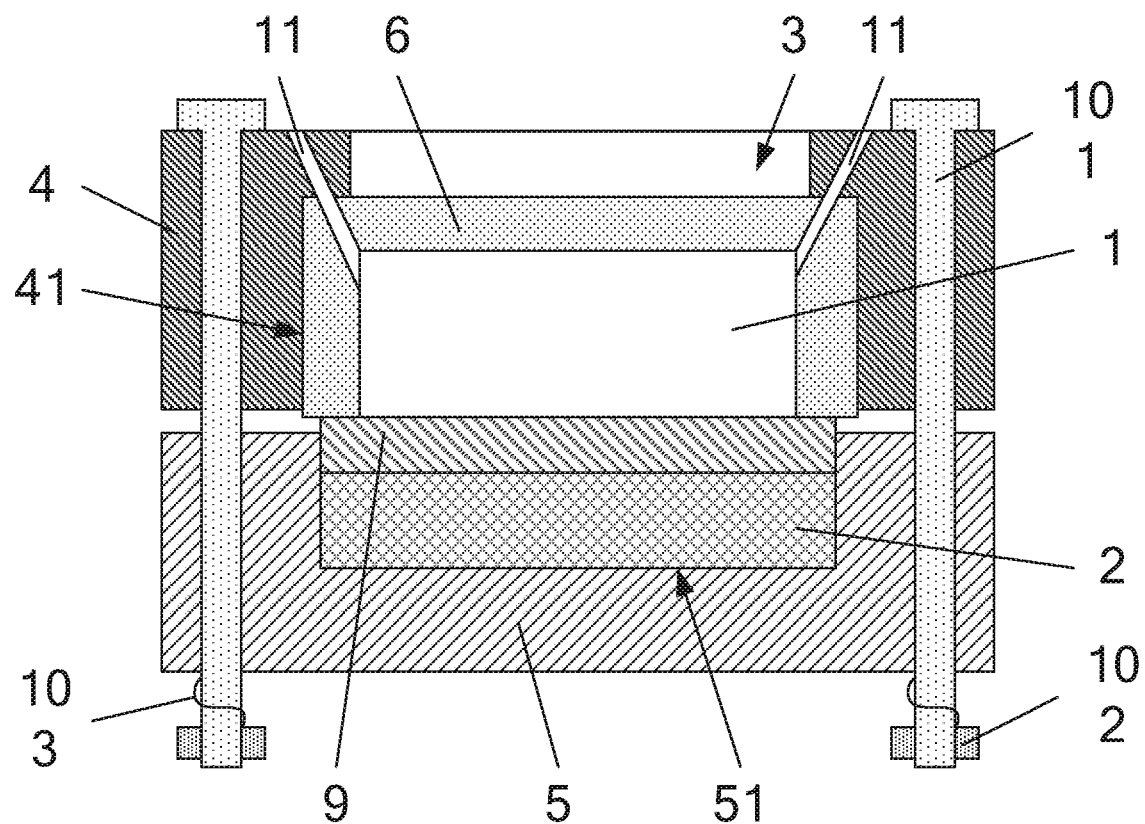
FIG. 5 is a sectional schematic view of an experimental apparatus for a biochip according to another embodiment of the present disclosure after a gene chip is mounted thereon.

Specifically, as shown in FIG. 1, FIG. 4 and FIG. 5, the observation area is a transparent observation window 3, the observation window 3 may be located on a top wall or a side wall of the chamber 1, and an experimenter may observe the reaction condition inside the chamber 1 through the observation window 3.

The experimental apparatus may further comprise: a constant temperature module 2 mounted on the enclosure and configured to keep a temperature within the chamber 1 to be constant during the experiment.

In the experimental apparatus, the constant temperature module 2 is mounted on the enclosure and configured to keep the temperature within the chamber 1 to be constant during the experiment, so as to improve temperature consistency of the chamber 1 during the experiment.

The experimental apparatus can be used for various biochips such as gene chips, protein chips, tissue chips, so that the biochip works under a proper temperature environment to better guarantee stability and reliability of the work of the biochip. When used in the work of a gene chip 9, genes on the gene chip 9 are hybridized with solutes in the solution, such that a better hybridization signal uniformity is obtained.

Specifically, the constant temperature module 2 includes a heat sink configured to keep the temperature within the chamber 1 to be constant. When heat energy is transferred to the heat sink, the temperature of the heat sink does not change with a magnitude of the heat energy transferred to the heat sink, to better keep temperature consistency of the chamber during the experiment. The material of the heat sink can be aluminum, copper or ceramic and the like, all of which can achieve the purpose of the application without departing from the design idea of the present disclosure, and repeated description of which is omitted herein but should also be within the protection scope of the present application. The heat sink can be connected with a heat energy supply device to transfer heat energy to the heat sink.

As shown in FIG. 1 and FIG. 5, a through hole 11 may be provided in a wall of the chamber 1, through which a solution can be filled, discharged, added, etc. into/from/to the chamber 1. Specifically, the through hole 11 includes a liquid inlet hole, a liquid outlet hole, and a liquid feeding hole, which may be provided in the top wall or the side wall of the chamber 1. The liquid inlet hole is used for filling the solution to the chamber 1, the liquid outlet hole is used for discharging the solution out of the chamber 1, and the liquid feeding hole is used for adding the solution to the chamber 1. Although only two through holes 11 are shown in the drawings, it will be understood by those skilled in the art that any number of through holes may be provided as desired. Moreover, the position of the through holes can vary as needed.

The enclosure may be a split structure, so that the enclosure thus manufactured has advantages such as simple structure, disassembly for cleaning, reuse, can reduce the experiment cost, and has a better practicability.

Specifically, as shown in FIG. 1, the enclosure comprises: a first pressing block 4 provided with a first reaction groove 41; and a second pressing block 5 provided with a second reaction groove 51, the first pressing block 4 and the second pressing block 5 fixed together, and the first reaction groove 41 and the second reaction groove 51 encircling to form the chamber 1.

Preferably, the enclosure further comprises: a sealing member mounted on one of the first reaction groove 41 and the second reaction groove 51, for pressing the biochip against the other of the first reaction groove 41 and the second reaction groove 51 during the experiment, and functioning as a seal during the experiment, to prevent the solution from leaking to the outside at a gap between the first reaction groove 41 and the second reaction groove 51. Moreover, the sealing member is an elastic buffer member that flexibly presses against the biochip to prevent the biochip from being crushed.

For example, as shown in FIGS. 1 and 5, the sealing member is a sealing cover 6, the constant temperature module 2 is mounted inside the second reaction groove 51, an opening is provided on a wall of the first reaction groove 41, the sealing cover 6 is mounted inside the first reaction groove 41 and covers the opening, the opening of the sealing cover 6 faces the second reaction groove 51, and the opening end of the sealing cover 6 presses the biochip against the constant temperature module 2 during the experiment, the solution is defined in the chamber formed by the encircling of the biochip and the sealing cover 6, and the opening can serve as an observation window 3 through which the reaction condition within the chamber 1 can be observed. Alternatively, an opening may be provided on the top wall of the second reaction groove 51, the sealing cover 6 is disposed within the second reaction groove 51, and the constant temperature module 2 is disposed within the first reaction groove 41, etc. which can also achieve the objective of the present application without departing from the design idea of the present disclosure, and repeated description of which is omitted herein but should be also within the protection scope of the present application.

Figure 2:
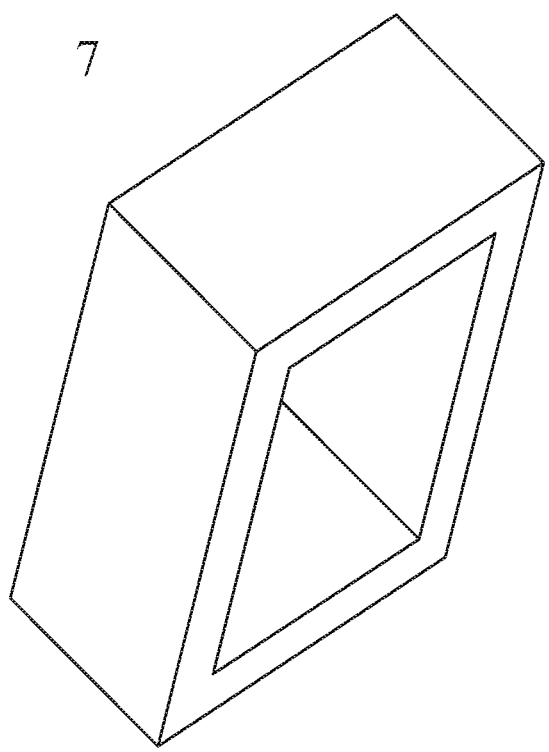
FIG. 2 is a perspective schematic view of the mounting cover of FIG. 1.
Figure 3:
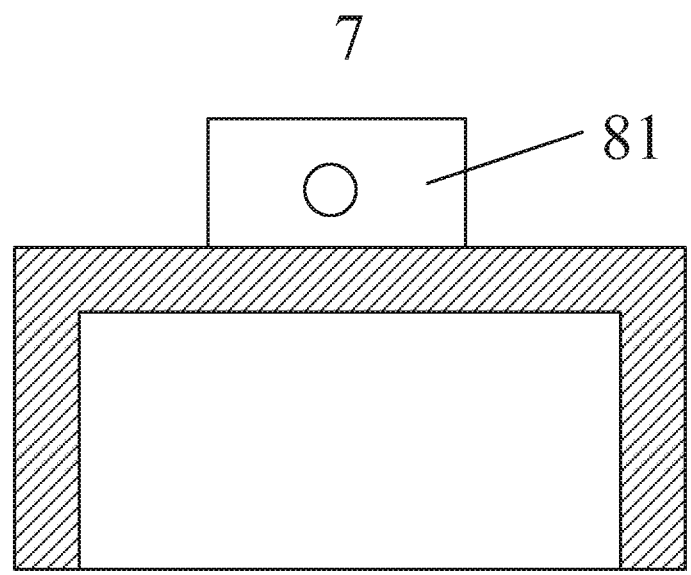
FIG. 3 is a sectional schematic view of the mounting cover of FIG. 2.

As shown in FIGS. 1 to 3, the enclosure may further comprise a mounting cover 7, an opening is provided on the wall of the first reaction groove 41, the mounting cover 7 is mounted within the first reaction groove 41 and covers the opening, the sealing cover 6 is mounted within the mounting cover 7, and the opening of the mounting cover 7 and the opening of the sealing cover 6 both face the second reaction groove 51. The mounting cover 7 is made of a transparent material such as glass, the sealing cover 6 is made of a transparent material such as rubber and epoxy resin, the opening can serve as the observation window 3, through which the reaction condition within the chamber 1 can be observed. Or, the top wall (i.e., the outward side) of the second reaction groove 51 may be provided with an opening, the mounting cover 7 and the sealing cover 6 both are disposed in the second reaction groove 51, and the constant temperature module 2 is disposed in the first reaction groove 41, etc., which can also achieve the purpose of the present application without departing from the design idea of the present disclosure, and repeated description of which is omitted herein but should also be within the protection scope of the present application.

Specifically, as shown in FIGS. 1 to 4, a positioning lug 81 is provided on the top wall of the mounting cover 7, the positioning lug 81 protrudes from the opening, a fitting lug 82 is provided on a wall of the opening, the fitting lug 82 is located outside the opening, and the positioning lug 81 and the fitting lug 82 are screwed together to fix the mounting cover 7 so that the mounting cover 7 is firmly positioned within the chamber 1. Moreover, the positioning lug 81 and the fitting lug 82 may include one or two sets correspondingly disposed, which can also achieve the purpose of the present application without departing from the design idea of the present disclosure, and repeated description of which is omitted herein but should also be within the protection scope of the present application.

For example, the fitting lug 82 may be integrally formed with the first pressing block 4, and the fitting lug 82 may also be fixed to the first pressing block 4 by means of screws or welding.

Specifically, as shown in FIGS. 1 and 5, the experimental apparatus further comprises: a plurality of bolts 101 mounted on the first pressing block 4 and the second pressing block 5 in a penetrating manner; and a plurality of springs 103 and a plurality of nuts 102, wherein the plurality of springs 103 are sleeved on the plurality of bolts 101 in a one-to-one correspondence manner, the plurality of nuts 102 are mounted on the plurality of bolts 101 in a one-to-one correspondence and rotation manner and pressed against each other through the plurality of springs 103 to fix the first pressing block 4 and the second pressing block 5 together, and the plurality of springs 103 can elastically adjust the pressure of the first pressing block 4 and the second pressing block 5, such that the pressure received in each position at the edge of the biochip is substantially the same and smaller, to prevent that a clamp force between the first pressing block 4 and the second pressing block 5 is too big or uneven to crush the biochip; the manufactured experimental apparatus has a better performance, and can better guarantee that the experiment goes on normally.

The experimental apparatus disclosed by the embodiments of the present disclosure basically has no interference from human factors on the detection result, so that the application level of the gene chip in the aspects of gene polymorphism analysis, disease diagnosis and the like can be improved.

In conclusion, the experimental apparatus for a biochip provided by the present disclosure can observe the reaction condition of the biochip and the solution through the observation area during the experiment, can perform real-time monitoring, and can observe the working process and result of the biochip without the need of taking out the biochip. Moreover, a volume of the chamber can be designed smaller, and an amount of the solution used during the experiment is then less, which can reduce the experiment cost.

In the description herein, the terms "mounted", "coupled", "connected", "fixed" and the like are intended to be broadly construed, and for example, "connected" may be fixedly, detachably, or integrally connected; may be directly connected or indirectly connected through an intermediate. Specific meanings of the above terms herein can be understood by those skill in the art as appropriate.

In the description of the specification, the terms "one embodiment", "some embodiments", "a specific embodiment" or the like mean that specific features, structures, materials, or characteristics described in connection with the embodiment or example are included in at least one embodiment or example herein. In this specification, schematic representations of the terms above do not necessarily refer to the same embodiment or example. Furthermore, the specific features, structures, materials, or characteristics described may be combined in any suitable manner in any one or more embodiments or examples.

Although the embodiments disclosed herein are described above, they are the embodiments used only for the convenience of understanding of the present disclosure and are not intended to limit the present disclosure. It will be understood by those skilled in the art that various modifications and changes in form and details may be made without departing from the spirit and scope of the present disclosure, and that the scope of patent protection of the present disclosure is to be limited only by the appended claims.

What is claimed is:

1. An experimental apparatus for a biochip, comprising:
   an enclosure within which a chamber configured to hold the biochip and a solution is disposed, wherein the enclosure is provided with an observation area, for observing a reaction process of the biochip and the solution in the chamber during an experiment,
   the enclosure comprises:
   a first pressing block, and
   a second pressing block opposing the first pressing block, wherein a side of the first pressing block facing the second pressing block is provided with a first reaction groove,
   a side of the second pressing block facing the first pressing block is provided with a second reaction groove,
   the first pressing block and the second pressing block are detachable and can be fixed together, and
   the first reaction groove and the second reaction groove encircle to form the chamber,
   wherein the experimental apparatus further comprises:
   a connecting member, one end of which penetrates through the first pressing block and the second pressing block, and the other end of which is provided with a limiting part; and
   a spring and a locking member, wherein the spring is sleeved on the connecting member, the locking member is fixed to the one end of the connecting member, and the spring presses against the first pressing block and the second pressing block to make the first pressing block and the second pressing block fixed together.

2. The experimental apparatus for a biochip according to claim 1, wherein the enclosure is a split structure.

3. The experimental apparatus for a biochip according to claim 1, wherein the enclosure further comprises:
   a sealing cover mounted within one of the first reaction groove and the second reaction groove, and having an opening end facing the other of the first reaction groove and the second reaction groove, wherein the biochip is pressed against the other of the first reaction groove and the second reaction groove through the opening end of the sealing cover during the experiment, and the chamber formed by the encircling of the sealing cover and the biochip is used to define the solution.

4. The experimental apparatus for a biochip according to claim 3, wherein the enclosure further comprises:
   a mounting cover mounted within the one of the first reaction groove and the second reaction groove, an opening of the mounting cover facing the other of the first reaction groove and the second reaction groove, and the sealing cover being mounted within the mounting cover.

5. The experimental apparatus for a biochip according to claim 4, wherein a positioning lug is arranged on the mounting cover, the positioning lug penetrates through one of the first pressing block and the second pressing block corresponding to the one of the first reaction groove and the second reaction groove to protrude out, a fitting lug is arranged on the corresponding one of the first pressing block and the second pressing block, and the positioning lug and the fitting lug are fixed together.

6. The experimental apparatus for a biochip according to claim 4, wherein the sealing cover is made of transparent epoxy resin, the mounting cover is made of transparent glass, and the observation area is an observation window located on one of the first pressing block and the second pressing block corresponding to the one of the first reaction groove and the second reaction groove.

7. The experimental apparatus for a biochip according to claim 1, further comprising:
   a constant temperature module mounted on the enclosure and configured to keep a temperature within the chamber to be constant during the experiment.

8. The experimental apparatus for a biochip according to claim 7, wherein the constant temperature module includes a heat sink mounted on a wall of the chamber and configured to keep the temperature within the chamber to be constant.

9. The experimental apparatus for a biochip according to claim 1, wherein the enclosure is provided with a through hole in communication with the chamber.

10. The experimental apparatus for a biochip according to claim 9, wherein the through hole includes at least one of a liquid inlet hole, a liquid outlet hole and a liquid feeding hole.

11. The experimental apparatus for a biochip according to claim 2, further comprising:
    a constant temperature module mounted on the enclosure and configured to keep a temperature within the chamber to be constant during the experiment.

12. The experimental apparatus for a biochip according to claim 3, further comprising:
    a constant temperature module mounted on the enclosure and configured to keep a temperature within the chamber to be constant during the experiment.

13. The experimental apparatus for a biochip according to claim 4, further comprising:
    a constant temperature module mounted on the enclosure and configured to keep a temperature within the chamber to be constant during the experiment.

14. The experimental apparatus for a biochip according to claim 5, further comprising:
    a constant temperature module mounted on the enclosure and configured to keep a temperature within the chamber to be constant during the experiment.

15. The experimental apparatus for a biochip according to claim 6, further comprising:
    a constant temperature module mounted on the enclosure and configured to keep a temperature within the chamber to be constant during the experiment.

* * * * *